United States Patent [19]

Candau et al.

[11] Patent Number: 5,629,004
[45] Date of Patent: May 13, 1997

[54] EMULSION CONTAINING STABILIZED ASCORBIC ACID, COSMETIC TREATMENT PROCESS USING IT AND USES THEREOF

[75] Inventors: Didier Candau, Bievres; Nathalie Collin, Sceaux, both of France

[73] Assignee: L'Oreal, Paris, France

[21] Appl. No.: 607,494

[22] Filed: Feb. 27, 1996

Related U.S. Application Data

[63] Continuation of Ser. No. 383,431, Feb. 3, 1995.

[30] Foreign Application Priority Data

Feb. 4, 1994 [FR] France .................................. 94 01282

[51] Int. Cl.$^6$ ........................................................ A61K 7/00
[52] U.S. Cl. .......................... 424/401; 514/844; 514/845; 514/846; 514/847
[58] Field of Search .......................... 424/401; 514/937, 514/938, 844–847; 549/315; 562/589

[56] References Cited

U.S. PATENT DOCUMENTS 5,162,378   11/1992   Guthauser ............................ 514/785

*Primary Examiner*—Thurman K. Page
*Assistant Examiner*—Sharon Howard
*Attorney, Agent, or Firm*—Oblon, Spivak, McClelland, Maier & Neustadt, P.C.

[57] ABSTRACT

An emulsion containing stabilized ascorbic acid, alone or as a mixture with another acid, such that the aqueous phase has an acidic pH, which is at most equal to 3.5, with the emulsion further containing an emulsifying agent formed of dimethiconecopolyol or alkyldimethiconecopolyol is provided along with its use in the cosmetics, dermatological and/or veterinary fields.

26 Claims, 1 Drawing Sheet

EMULSION CONTAINING STABILIZED ASCORBIC ACID, COSMETIC TREATMENT PROCESS USING IT AND USES THEREOF

This is a Continuation of application Ser. No. 08/383,431 filed on Feb. 3, 1995, pending.

BACKGROUND OF THE INVENTION

1. Field of the Invention

The present invention relates to a water-in-oil (W/O) emulsion containing stabilized ascorbic acid, which is useful in the cosmetic, dermatological and/or veterinary fields, and methods for using these emulsions in the cosmetic treatment of the skin as well as for the preparation of a cream or ointment intended for the dermatological treatment of the skin and/or for veterinary treatment.

2. Discussion of the Background

Workers have long sought to stabilize ascorbic acid, or vitamin C, in suitable pharmaceutical forms, on account of its beneficial properties.

Indeed, ascorbic acid has many known biological functions, such as the stimulation of collagen synthesis, the strengthening of skin tissues against external attack (UV radiation, pollution), depigmentation, activity against free radicals and the compensation for vitamin E deficiency. Some of these beneficial properties have been reported in particular by England and Seifter in the article "The biochemical functions of ascorbic acid" published in Ann. Rev. Nutri., 1986: 6, pp 365–406.

However, owing to its chemical structure (alpha-keto lactone), ascorbic acid is very sensitive to the influence of environmental parameters such as light, oxygen and water (due to its pH and due to the presence of traces of metals). An unavoidable degradation of ascorbic acid in solution occurs over time.

This problem has been addressed in a variety of ways in the art.

In order to reduce or delay the degradation of ascorbic acid in solution, US-A-5,140,043 recommends stabilization by introducing ascorbic acid into aqueous-alcoholic solutions, formed of at least 80% water and having a pH below 3.5.

On account of the high acidity of these solutions, their use in the cosmetic and/or pharmaceutical field is not readily conceivable. Indeed, repeated application of these solutions may disrupt the equilibrium of the skin and may in particular irritate, or even burn, the skin.

Moreover, B. R. Hajratwala, in "Stability of ascorbic acid", published in the Revue Sciences Pharmaceutiques on 15 Mar., 1905, teaches that ascorbic acid may be stabilized as an acidic aqueous solution by adding a surface-active agent which is an oxyethylenated sorbitan ester.

In particular, Hajratwala states that at pH=3.4 and 25° C., the addition of this agent reduced the rate of oxidation, and thus the rate of degradation, of ascorbic acid in solution.

Hajratwala also teaches the use of a chelating agent such as ethylenediaminetetraacetic acid (EDTA) and packaging under nitrogen, in the absence of light, in order to enhance the stability of the aqueous ascorbic acid solution.

However, such an acidic aqueous solution, applied to the skin, has the same drawbacks as those described above for acidic aqueous-alcoholic solutions. Furthermore, the stabilization obtained is still insufficient.

Other ways of stabilizing ascorbic acid have been proposed, in particular by a coating technique (FR-A-1,600, 826) or by granulation of ascorbic acid (JP-A-53-127,819) for the agri-foods industry.

However, these techniques are, on the one hand, expensive and may, on the other hand, damage the ascorbic acid, for example during heating, and/or may lead to compositions of poor cosmetic acceptability, as in the case of granules.

Moreover, FR-A-1,489,249 discloses the use of metal salts of phosphorylated ascorbic acid, in particular magnesium ascorbylphosphate, in cosmetic compositions.

The latter compound has an activity close to that of ascorbic acid, from which it is derived, but it has certain drawbacks which render its use on the skin unfeasible. In particular, since magnesium ascorbylphosphate is only stable at basic pH (pH 8 to pH 9), it must be incorporated into a basic composition which may be irritant to the skin (the pH of which is about 5.5).

Consequently, none of the previous proposals have made it possible to overcome the technical problem associated with the instability of ascorbic acid in solution, in a pharmaceutical form which is suitable for the cosmetic and/or dermatological fields and at a cost which is compatible with industrial requirements.

SUMMARY OF THE INVENTION

Accordingly, one object of the present invention is to provide a composition, which may be used in the cosmetic, dermatological and/or veterinary fields, containing stabilized ascorbic acid, in the free state, (i.e. without an additional, especially stabilizing, group), and which does not cause any skin irritation after application.

Another object of the present invention is to provide a cosmetic, dermatological and/or veterinary composition in the form of an emulsion.

A further object of the present invention is to provide a method for using the above emulsion for the cosmetic treatment of the skin and in particular in order to smooth out the fine lines in the skin, to tone and regenerate the skin, in order to lighten the complexion, to remove blemishes from the skin, in order to combat the harmful effects of UV radiation, and/or in order generally to strengthen skin tissues against environmental attacks (pollution).

Another object of the present invention is the use of the above emulsion for the manufacture of a cream intended for a dermatological and/or veterinary treatment.

A further object of the present invention is to provide a cosmetic treatment process which consists of application to the skin, including application around the eyes, of an emulsion in accordance with the invention.

These and other objects of the present invention have been satisfied by the discovery of an emulsion comprising an aqueous phase dispersed in an oily phase using an emulsifying agent, wherein the aqueous phase comprises ascorbic acid and has an acidic $pH \leq 3.5$, and wherein the emulsifying agent is a dimethiconecopolyol, an alkyldimethiconecopolyol or a mixture thereof, wherein the ascorbic acid is stabilized by inclusion in the aqueous phase.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
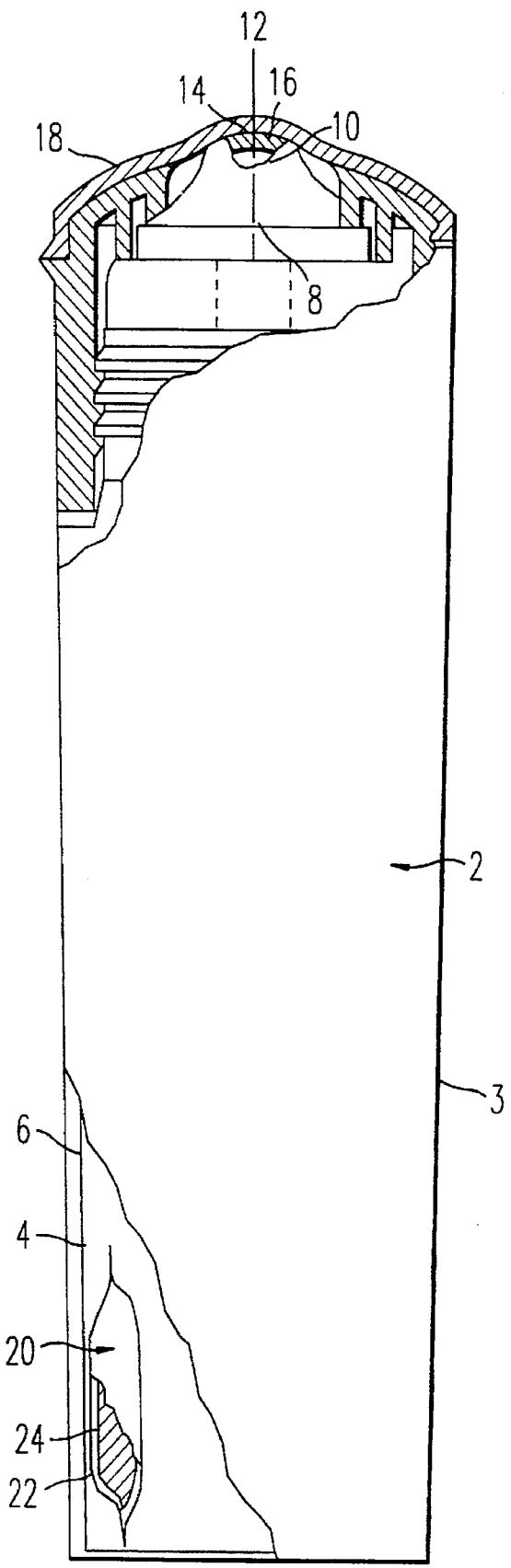
FIG. 1 represents an example of packaging which is compatible with the emulsion according to the invention.

The present invention relates to an emulsion, comprising an aqueous phase dispersed in an oily phase using an emulsifying agent, wherein the aqueous phase contains stabilized ascorbic acid and has an acidic pH≦3.5 and wherein that the emulsifying agent is a dimethiconecopolyol and/or an alkyldimethiconecopolyol.

In the present description, the emulsifying agent used in the invention is defined according to the CTFA nomenclature.

The advantage of using the W/O emulsion of the present invention lies especially in the fact that the acidic aqueous phase, containing the ascorbic acid, is in a small amount on the skin, in the form of fine droplets dispersed in the oil, thereby causing no irritation or burning of the skin. Consequently, the emulsion of the invention is well tolerated by users, contrary to the case for solutions.

The concentrations of ascorbic acid in the emulsions of the present invention are those conventionally used in the cosmetics field and are preferably from 0.1 to 10%, and most preferably from 0.5% to 5%, by weight relative to the total weight of the emulsion.

Moreover, the fact that the emulsion of the present invention incorporates ascorbic acid in the free, protonated state provides treatments which are more effective when compared with the preparations of the prior art which contain ascorbic acid derivatives that may be hydrolyzed on contact with the skin.

The emulsions of the present invention may be provided in the form of a milk or a cream, and may be used in particular in the cosmetics, dermatological and/or veterinary fields. The present emulsions have a light texture and spread well. Furthermore, on application, they give a sensation of freshness and provide an immediate glowing complexion. They enable, in particular, the marks and imperfections of the skin to be smoothed out.

In addition, the emulsions in accordance with the present invention have the advantage of being able to include any type of acid-insensitive hydrophilic or lipophilic active agent other than ascorbic acid.

The emulsions of the present invention further contain a dimethiconecopolyol and/or alkyldimethiconecopolyol as an emulsifying agent. This provides the present emulsion with higher stability at room temperature (20° C.), than emulsions containing other types of emulsifying agent.

This emulsifying agent preferably comprises totally oxyethylenated polyether groups, but it is possible to use partially oxyethylenated emulsifying agents.

Preferably, the percentage by weight of polyether relative to the total weight of the emulsifying agent is chosen from 1% to 50%, more preferably from 15% to 35% in the case of dimethiconecopolyols, and preferably from 1% to 5%, more preferably from 2% to 3%, in the case of alkyldimethiconecopolyols.

A dimethiconecopolyol which may be mentioned is the product sold under the name Q2-3225C by the Dow Corning company. However, the product sold under the name SF-1228 by the General Electric company is preferably used.

An alkyldimethiconecopolyol that may be used is lauryldimethiconecopolyol which is sold, for example, under the name Q2-5200 by the Dow Corning company. However, cetyldimethiconecopolyol which is sold, for example, under the name ABIL EM 90 by the Goldschmidt company is preferably used.

The emulsifying agents which may be used in the emulsion of the present invention may also be combined with at least one co-emulsifying agent such as polyglycerol tetraisostearate or polyglycerol trioleate.

In practice, these emulsifying agents are present in an amount from 1% to 10%, and preferably from 2.5% to 3.5%, by weight relative to the total weight of the emulsion when they are used alone. When the content of emulsifying agent is chosen below 2.5% by weight relative to the total weight of the emulsion, it is preferable to add a co-emulsifying agent. When it in present, the co-emulsifying agent is used in an amount of 1 to 10 times the amount of the emulsifying agent. The respective concentrations of emulsifying agents and co-emulsifying agents are preferably chosen to be from 0.5% to 2.2% and from 3% to 7% by weight relative to the total weight of the emulsion.

For storage at temperatures above 20° C. and/or for long periods of storage of several months, it is preferred to use a totally oxyethylenated alkyldimethiconecopolyol, and more preferably cetyldimethiconecopolyol, as the emulsifying agent.

In order to keep the pH of the aqueous phase of the present emulsions acidic for long periods, a stable additional acid is advantageously combined with the ascorbic acid. This acid may be any acid which makes it possible to obtain the desired acidic buffering effect. This additional acid is preferably an α-hydroxy acid chosen from lactic acid, glycolic acid and citric acid.

Indeed, this particular type of acid has the additional advantage, when it is applied to the skin, of removing the dead cells of the epidermis by its keratolytic action and of promoting the penetration of other active agents, such as the ascorbic acid of the present invention.

Other acids which may in particular be used are β-hydroxy acids or acetic acid.

The amount of acid in the present emulsions, whether ascorbic acid alone or as a mixture with an additional acid, should be sufficient to obtain an acidic pH value, preferably, a pH from 1.5 to 3.5, most preferably from 1.8 to 2.7.

In order to achieve the most preferred pH values (1.8 to 2.7), ascorbic acid, if it is used alone, should be present at a concentration above 4% by weight relative to the total weight of the emulsion.

According to the invention, the aqueous phase of the emulsion may represent from 60% to 80%, and preferably from 65% to 75%, by weight relative to the total weight of the emulsion. Below 60%, oil may be released therefrom and the emulsion is then no longer homogenous. Above 80%, the emulsion obtained is harder to spread on the skin due to its viscosity.

The aqueous phase of the emulsions of the present invention may additionally contain an electrolyte, such as sodium chloride or potassium chloride, in order to further stabilize the emulsion.

The content of electrolyte, when present, is generally from 0.5% to 2% by weight relative to the total weight of the emulsion.

In order to avoid the presence in the aqueous phase of heavy metals which may catalyze the degradation of the ascorbic acid, the aqueous phase is preferably formed using exchanged or deionized water.

In order to further increase the stability of ascorbic acid over time, the present emulsions may comprise a metal-sequestering agent such as a phosphonic acid derivative.

The phosphonic acid derivatives which may be used in the invention include ethylenediaminetetra (methylenephosphonic) acid, hexamethylenediaminetetra (methylenephosphonic) acid, diethylenetriaminepenta (methylenephosphonic) acid and the salts thereof, preferably the sodium salts thereof, such as the pentasodium salt of ethylenediaminetetra (methylenephosphonic) acid.

Ethylenediaminetetra (methylenephosphonic) acid, which is sold in particular by the Monsanto company under the name Dequest 2041, is most preferably used. It is also possible to use the pentasodium salt of this acid, which is sold under the name Dequest 2046 by the Monsanto company. As another sequestering agent which may be used in the emulsions of the present invention, there may be mentioned diethylenetriaminepentaacetic acid, which is sold by the Sigma company.

The choice of metal-sequestering agent is not immaterial. It is known that, in the presence of iron, ethylenediaminetetraacetic acid (EDTA) has a pro-oxidizing effect and thus a destabilizing effect an ascorbic acid, which effect is undesirable. This effect has been observed in the present emulsions when the metal-sequestering agent is insufficient in activity.

When it is present, the sequestering agent is at a concentration ranging from 0.05% to 0.2% by weight relative to the total weight of the emulsion.

The oily phase of the present emulsions may contain any kind of oils and fatty substances that are well known to those skilled in the art, such as mineral oils, organic oils, plant oils or synthetic oils, oils which may or may not contain silicone, and in particular volatile silicone oils, a liquid fraction of Shea butter (palmitic, stearic, oleic and linoleic acid triglycerides), almond oil, apricot oil, a mixture of cetylstearyl 2-ethylhexanoate and isopropyl myristate, and synthetic perhydrosqualene.

The oily phase of the emulsions of the present invention preferably comprises a volatile silicone-containing oil in an amount of 3% to 15% by weight relative to the total weight of the emulsion. A suitable volatile silicone containing oil is a cyclic silicone such as cyclopentadimethylsiloxane. This silicone is sold in particular by the Dow Corning company under the name $D_5$. It in also possible to use any other volatile silicone-containing oil, such as cyclohexadimethylsiloxane sold under the name $D_6$ by the Dow Corning company.

The oily phase may additionally comprise a gelling agent, usually in an amount of 1% to 15%, preferably 3% to 7%, of the total weight of the emulsion. When it is present, this gelling agent may be, in particular, a derivative of a hectorite-type clay, such as that sold under the name Simagel Si 345 by the Stearineries Dubois company.

The emulsions of the present invention may finally comprise any acid-insensitive additive which is compatible with the intended application.

This additive, when it in present, is especially at a concentration which is commonly accepted in the intended field, depending in particular on its degree of solubility. This concentration may generally be chosen from 0.01% to 30% by weight relative to the total weight of the emulsion.

Suitable additives include hydrophilic or lipophilic active agents, lipid-soluble emollients, preserving agents, fragrances, fillers and dyes, on condition, of course, that the additive does not destabilize the ascorbic acid in the emulsion.

When it is present, the lipid-soluble emollient may in particular be a silicone gum, for instance a mixture of cyclopentadimethylsiloxane and dimethiconol, for the softness provided thereby.

The active agents which may preferably be used in the invention comprise moisturizing agents, such as glycerol, sodium pyrrolidonecarboxylate, NMFs (normal moisturizing factors) and hyaluronic acid.

Other active agents may be used, such as UV screening agents, proteins or protein hydrolysates, plant extracts and essential oils.

The emulsion of the invention may be applied topically to the face, which includes application around the eyes, to the body and to the scalp of humans.

The composition of the invention preferably comprises, by weight:

from 0.5% to 5% of ascorbic acid,
from 2.5% to 3.5% of cetyldimethiconecopolyol,
from 3% to 15% of volatile silicone-containing oil,
from 0.01% to 0.1% of the pentasodium salt of ethylenetetra (methylenephosphonic) acid, and
from 0.5% to 2% of sodium chloride.

As already mentioned above, ascorbic acid is unstable in the presence of light and oxygen. For this reason, it is preferable for the emulsion according to the invention to be packaged so as not to be in contact with oxygen and so as to be protected from the light.

Thus, the emulsion of the invention is preferably prepared under an inert atmosphere (nitrogen or a rare gas such as argon), which is free of oxygen, and under inactinic light, such as that of a sodium vapor lamp.

The emulsion of the invention is advantageously packaged in the presence of an oxygen trap. This trap is preferably separated from the emulsion by a gas-porous and liquid-impermeable membrane.

As an example of an oxygen trap which may be used in the emulsion according to the invention, there may be mentioned the Atco oxygen trap sold by the Standa Industries company.

As a gas-porous and liquid-impermeable membrane which may be used in the present invention, there may be mentioned that described in FR-A-2,671,055.

Even more preferably, the emulsion of the invention is packaged in a container surmounted by a dispensing device with no air inlet such as that described in FR-A-2,666,308.

FIG. 1 represents an example of packaging which is compatible with the emulsion according to the invention.

The packaging (2) is composed of a container (3), the walls (4) of which consist of any gas-impermeable material which may be made, for example, of a thermoformed material or of any other suitable material on condition that the inner surface of the walls, in contact with the emulsion (6), is not metallic and that this material does not allow light to pass through.

The container (3) is surmounted by an air dispensing device (8) consisting of a dome which is convex towards the exterior (10) and of at least one slot (12) provided in the top of the dome.

The walls (14, 16) of the slot (12) are able to come into contact with each other in order to achieve leaktight sealing, when at rest. The whole device (8) is surmounted by an airtight cap (10) which provides a double protection for the emulsion of the invention with respect to the environment.

A pocket (20), independent of the packaging, the walls (22) of which pocket are formed of a gas-porous and liquid-impermeable membrane, contains an oxygen trap (24). The membrane (22) may be formed of a material chosen from polyethylene, propylene and polyethylene/terephthalate.

When at rest, the walls (14, 16) of the dome are in close contact, which thus provides the leaktightness for the slot (12). By exerting pressure on the packaging (2), pressure is transmitted to the emulsion of the invention, which will tend to separate the walls (14, 16), thus enabling the emulsion to come out of the packaging. When the pressure is released, the walls (14, 16) return to their rest position and close the slot (12) by obstruction.

Having generally described this invention, a further understanding can be obtained by reference to certain specific examples which are provided herein for purposes of illustration only and are not intended to be limiting unless otherwise specified.

EXAMPLES

The compositions of the present invention which follow were obtained according to the following procedure.

The following steps 1 to 3 were performed successively in a glove box and under a nitrogen atmosphere, working permanently by degassing as well as in the presence of inactinic light and at room temperature (20° C.):

1) The constituents of the aqueous phase (A) were dissolved with moderate stirring, followed by addition of ascorbic acid which was predissolved by stirring with a magnetic bar immediately prior to making the emulsion.

2) Meanwhile, the constituents of the oily phase (B) were mixed together.

3) Phase (A) was then poured into phase (B) and the mixture was stirred vigorously by shearing using a Moritz-type mixer for 1 min to 10 min, followed by gentle stirring with a paddle, in order to obtain an emulsion according to the invention which took the form, in particular, of a cream.

In these W/O emulsions stored for at least 2 months at room temperature, no degradation of the ascorbic acid was observed. Thus, the ascorbic acid was indeed stabilized.

For longer periods of storage, the ascorbic acid in these emulsions was also shown to be particularly stable and the percentage of degradation thereof proved to be markedly lower than those of the prior art.

Moreover, a degradation of only 10% to 20% of the ascorbic acid was observed after storage for two months at a temperature as high as 45° C.

EXAMPLE 1

Face Cream

| | |
|---|---|
| Cetyldimethiconecopolyol | 3 |
| Cyclopentadimethylsiloxane | 12 |
| Mixture of cetylstearyl 2-ethylhexanoate and isopropyl myristate (90/10) | 3 |
| Palmitic, stearic, oleic and linoleic acid triglycerides (5/25/60/10) | 2 |
| Hectorite modified with distearyldimethylammonium chloride, dispersion in cyclopentadimethlylsiloxane and ethanol (15/80/5) | 5 |
| Pentasodium salt of ethylenetetra(methylenephosphonic) acid at a concentration of 33% in water | 0.1 |
| Sodium chloride | 0.7 |
| Lactic acid | 4 |
| Ascorbic acid | 1 |
| Preserving agents (diazolidinylurea) | 0.2 |
| (butyl paraben/sorbic acid) | 0.4 |
| Fragrance | 0.3 |
| Exchanged water q.s | 100 |

This face care cream had a thick texture. It was nourishing and spread gently. It provided an immediate glowing complexion and allowed imperfections to be smoothed out.

EXAMPLE 2

Clear Body Cream

| | |
|---|---|
| Dimethiconecopolyol/cyclopentadimethylsiloxane (10/90) | 25 |
| Hectorite modified with distearyldimethylammonium chloride, dispersion in cyclopentadimethylsiloxane and ethanol (15/80/5) | 5 |
| Pentasodium salt of ethylenetetra(methylenephosphonic) acid at a concentration of 33% in water | 0.1 |
| Sodium chloride | 0.7 |
| Glycolic acid | 4 |
| Ascorbic acid | 1 |
| Preserving agents(diazolidinylurea) | 0.2 |
| (butyl paraben/sorbic acid) | 0.4 |
| Fragrance | 0.3 |
| Exchanged water q.s | 100 |

This clear body cream spread very lightly and penetrated immediately into the skin. It toned, regenerated and nourished the skin of the body.

EXAMPLE 3

Cream For Greasy Skins

| | |
|---|---|
| Cetyldimethiconecopolyol | 1 |
| Triglyceryl tetraisostearate | 5 |
| Cyclopentadimethylsiloxane | 9 |
| Cyclohexadimethylsiloxane | 4 |
| Apricot oil | 3 |
| Mixture of cyclopentadimethylsiloxane and dimethiconol (90/10) | 4 |
| Glycerine | 5 |
| Glycolic acid | 4 |
| Ascorbic acid | 0.01 |
| Sodium chloride | 0.7 |
| Preserving agents (diazolidinylurea) | 0.2 |
| (butyl paraben/sorbic acid) | 0.4 |
| Fragrance | 0.3 |
| Exchanged water q.s. | 100 |

This cream for greasy skins was fluid in texture. It was slippery and light on spreading, and smoothed out marks. It provided a glowing complexion.

EXAMPLE 4

Cream For Normal Skins

| | |
|---|---|
| Cetyldimethiconecopolyol | 2 |
| Triglyceryl trioleate | 5 |
| Cyclopentadimethylsiloxane | 8 |
| Cyclohexadimethylsiloxane | 4 |
| Mixture of cyclopentadimethylsiloxane and dimethiconol (90/10) | 4 |
| Apricot oil | 3 |
| Glycerine | 3 |
| Ascorbic acid | 5 |
| Sodium chloride | 0.5 |
| Preserving agents (diazolidinylurea) | 0.2 |
| (butyl paraben/sorbic acid) | 0.4 |
| Fragrance | 0.3 |
| Exchanged water q.a | 100 |

This care cream for normal skin was very comfortable and formed a film after application. It provided a glowing complexion while at the same time allowing the imperfections of the skin to be smoothed out.

Obviously, numerous modifications and variations of the present invention are possible in light of the above teachings. It is therefore to be understood that within the scope of the appended claims, the invention may be practiced otherwise than as specifically described herein.

What is claimed as new and is desired to be secured by Letters Patent of the United States is:

1. An emulsion comprising an aqueous phase dispersed in an oily phase using an emulsifying agent, wherein said aqueous phase comprises ascorbic acid and has an acidic pH≦3.5, and wherein said emulsifying agent is a dimethiconecopolyol, an alkyldimethiconecopolyol or a mixture thereof, said emulsion comprising ascorbic acid, which is stable for at least two months at room temperature.

2. The emulsion according to claim 1, wherein the ascorbic acid in present in an amount from 0.5% to 5% by weight relative to the total weight of the emulsion.

3. The emulsion according to claim 1, further comprising an additional acid different from ascorbic acid.

4. The emulsion according to claim 3, wherein said additional acid different from ascorbic acid is a member selected from the group consisting of α-hydroxy acids, β-hydroxy acids and acetic acid.

5. The emulsion according to claim 1, wherein said aqueous phase has a pH from 1.5 to 3.5.

6. The emulsion according to claim 5, wherein said pH is from 1.8 to 2.7.

7. The emulsion according to claim 4, wherein said additional acid different from ascorbic acid is an α-hydroxy acid.

8. The emulsion according to the claim 7, wherein said α-hydroxy acid is lactic acid.

9. The emulsion according to claim 1, wherein said aqueous phase represents from 60% to 80% by weight relative to the total weight of the emulsion.

10. The emulsion according to claim 9, wherein said aqueous phase represents from 65% to 75% by weight relative to the total weight of the emulsion.

11. The emulsion according to claim 1, wherein said emulsifying agent is present in an amount of 1% to 10% by weight relative to the total weight of the emulsion.

12. The emulsion according to claim 1, wherein said emulsifying agent contains totally oxyethylenated polyether groups.

13. The emulsion according to claim 1, wherein said emulsifying agent in an alkyldimethiconecopolyol, having a percentage by weight of polyether groups of 2.5% relative to the total weight of alkyldimethiconecopolyol.

14. The emulsion according to claim 1, wherein said emulsifying agent is an alkyldimethiconecopolyol, having a $C_{16}$ alkyl group.

15. The emulsion according to claim 1, wherein said emulsifying agent is a dimethiconecopolyol, having a percentage by weight of polyether groups of 25% relative to the total weight of dimethiconecopolyol.

16. The emulsion according to claim 1, further comprising a co-emulsifying agent used in an amount which is 1 to 10 times the amount of the emulsifying agent.

17. The emulsion according to claim 1, further comprising a metal-sequestering agent.

18. The emulsion according to claim 17, wherein said sequestering agent is pentasodium ethylenediaminetetra (methylenephosphonic) acid.

19. The emulsion according to claim 1, wherein said emulsion is packaged so as not to be in contact with oxygen or with metal elements and so as to be protected from light.

20. The emulsion according to claim 1, wherein said emulsion is packaged in the presence of an oxygen trap which is separated from the emulsion by a gas-porous and liquid impermeable membrane.

21. An emulsion comprising, by weight:
from 0.5% to 5% of ascorbic acid,
from 2.5% to 3.5% of cetyldimethiconecopolyol,
from 3% to 15% of volatile silicone-containing oil,
from 0.01% to 0.1% of pentasodium ethylenetetra (methylenephosphonic) acid, and
from 0.5% to 2% of sodium chloride.

22. The emulsion according to claim 1, wherein said emulsifying agent is present in an amount of 2.5% to 3.5% by weight relative to the total weight of the emulsion, in the absence of a co-emulsifying agent.

23. The emulsion according to claim 1, wherein said emulsifying agent is at a content below 2.5%, in the presence of a co-emulsifying agent.

24. A composition suitable for use in the cosmetic dermatological or veterinary fields or any combination thereof, comprising an emulsion comprising an aqueous phase dispersed in an oily phase using an emulsifying agent, wherein said aqueous phase comprises ascorbic acid and has an acidic pH≦3.5, and wherein said emulsifying agent is a dimethiconecopolyol, an alkyldimethiconecopolyol or a mixture thereof, wherein said ascorbic acid is stable for at least two months at room temperature.

25. A method for cosmetic treatment of the skin in order to tone and regenerate it, to smooth out fine lines in the skin, to lighten skin complexion, to remove blemishes from the skin, in order to combat the harmful effects of UV radiation, in order to strengthen skin tissues against environmental attacks, or a combination thereof, comprising applying to the skin of a subject in need thereof, an effective amount of an emulsion comprising an aqueous phase dispersed in an oily phase using an emulsifying agent, wherein said aqueous phase comprises ascorbic acid and has an acidic pH≦3.5, and wherein said emulsifying agent is a dimethiconecopolyol, an alkyldimethiconecopolyol or a mixture thereof, wherein said ascorbic acid is stable for at least two months at room temperature.

26. A cream for dermatological or veterinary use or both, comprising an emulsion comprising an aqueous phase dispersed in an oily phase using an emulsifying agent, wherein said aqueous phase comprises ascorbic acid and has an acidic pH≦3.5, and wherein said emulsifying agent is a dimethiconecopolyol, an alkyldimethiconecopolyol or a mixture thereof, wherein said ascorbic acid is stable for at least two months at room temperature in a dermatologically or veterinarially acceptable cream base.

* * * * *

UNITED STATES PATENT AND TRADEMARK OFFICE
CERTIFICATE OF CORRECTION

PATENT NO. : 5,629,004
DATED : MAY 13, 1997
INVENTOR(S) : DIDIER CANDAU, ET AL.

It is certified that error appears in the above-identified patent and that said Letters Patent is hereby corrected as shown below:

Column 4, line 11, "When it in present,"

should read --When it is present,--.

Column 5, line 18, "destabilizing effect an ascorbic"

should read --destabilizing effect on ascorbic--.

Column 5, line 40, "It in also"

should read --It is also--.

Column 9, line 14, "acid in present"

should read --acid is present--.

Signed and Sealed this

Twenty-eighth Day of April, 1998

Attest:

BRUCE LEHMAN

Attesting Officer

Commissioner of Patents and Trademarks